United States Patent [19]
Winberry et al.

[11] Patent Number: 5,594,185
[45] Date of Patent: Jan. 14, 1997

[54] SELF-CONTAINED, MODULAR LYSIMETER AND METHOD OF USING THE SAME

[75] Inventors: Martin W. Winberry; Ranga R. Velagaleti; Mark D. Williams; Donna Daly, all of Columbia, Mo.; Len R. Swain, Raleigh; Jerome B. Weber, Wake Forest, both of N.C.

[73] Assignee: Analytical Bio Chemistry Laboratories, Inc., Columbia, Mo.

[21] Appl. No.: 473,732

[22] Filed: Jun. 7, 1995

[51] Int. Cl.$^6$ ............................................. G01N 1/00
[52] U.S. Cl. ................................. 73/866; 73/863.52
[58] Field of Search .................... 73/863.31, 863.41, 73/863.51, 863.52, 864.31, 866

[56] References Cited

U.S. PATENT DOCUMENTS

| | | |
|---|---|---|
| D. 269,844 | 7/1983 | Hackerson . |
| 3,324,958 | 6/1967 | Clark . |
| 3,407,607 | 10/1968 | Jordan . |
| 3,444,938 | 5/1969 | Ballmann . |
| 3,872,935 | 3/1975 | Mielke . |
| 3,978,932 | 9/1976 | Mielke . |
| 4,166,720 | 9/1979 | Weber . |
| 4,653,336 | 3/1987 | Vollweiler . |
| 4,692,287 | 9/1987 | Timmons . |
| 4,709,584 | 12/1987 | Voll et al. . |
| 4,759,227 | 7/1988 | Timmons . |
| 4,844,813 | 7/1989 | Helfgott et al. . |
| 4,923,333 | 5/1990 | Timmons . |
| 5,000,051 | 3/1991 | Bredemeier . |
| 5,009,112 | 4/1991 | Lawrence et al. . |
| 5,279,151 | 1/1994 | Coody et al. ............ 73/863.52 |
| 5,307,589 | 5/1994 | Rigsby . |
| 5,322,133 | 6/1994 | Hart . |

OTHER PUBLICATIONS

Letter dated Jan. 4, 1994 and drawings from Dr. Thompson of American Agricultural Services Inc.
Article "Variation in Soils with Respect to the Disposition of Natural Precipitation" by Stauffer and Smith; vol. 29 1937.
Article "A Device for Measuring Precipitation Waters Lost from the Soil as Surface Runoff . . . " by Musgrave.
Article "A Microlysimeter Field Study of Solute Transport . . . " by Richter and Jury. Computer generated search printout.

Primary Examiner—Robert Raevis
Attorney, Agent, or Firm—Stinson, Mag & Fizzell, PC

[57] ABSTRACT

The present invention comprises a self-contained, modular unit and method of using the same for evaluating the mobility, dissipation and degradation of chemicals and their degradates through a soil matrix. The self-contained, modular unit comprises at least a soil matrix vessel for containing the soil matrix and a leachate collection vessel communicating with the soil matrix vessel for collecting and storing the leachate from the soil matrix vessel. The leachate collection vessel is designed and connected to the soil matrix vessel in such a manner that the collected leachate is observable and removable at ground level, thus eliminating the necessity of digging a trench to view or retrieve the leachate as prior art units required. The preferred embodiment of the self-contained modular unit further comprises a runoff collection vessel which communicates with the soil matrix vessel and collects the runoff from the soil matrix vessel. By collecting both the runoff and the leachate, the user has the opportunity to perform a more complete analysis of the degradation and movement of the test chemicals and their degradates. Furthermore, if radiolabeled test chemicals are utilized, they are fully contained within the preferred embodiment of the self-contained modular unit of this invention.

15 Claims, 2 Drawing Sheets

SELF-CONTAINED, MODULAR LYSIMETER AND METHOD OF USING THE SAME

BACKGROUND OF THE INVENTION

1. Field of the Invention

The invention relates to a self-contained, modular unit and method of using the same for analyzing the mobility, dissipation, and degradation of chemicals and their degradates in the soil.

2. Background Information

With the protection of the environment becoming an ever increasing issue, applying chemicals to the soil is becoming less and less desirable, unless it is first determined that the chemicals will not adversely affect the surrounding soil, crops and plants, as well as the ponds, streams, rivers, and ground water into which the chemicals and their degradates ultimately flow. In fact, new pesticides, herbicides, and other agrochemicals must meet certain guidelines before they may be sold.

Investigating soil characteristics is not new. For example, G. W. Musgrave investigated the loss of precipitation from soil in 1935 which was documented in his paper entitled "A Device for Measuring Precipitation Waters Lost from the Soil As Surface Runoff, Percolation, Evaporation, and Transpiration." Musgrave collected both the leachate and runoff via an intricately developed system of interrelated soil cores and trenches. The soil cores were obtained and removed to a test site which had been built with special piping and trenches to collect the runoff and leachate. Similar tests were run in 1937 by R. S. Stauffer and R. S. Smith. Their tests were documented in their paper entitled, "Variation in Soils with Respect to the Disposition of Natural Precipitation."

The testing of soil characteristics has since evolved past the testing of only loss of precipitation to testing the dissipation of test chemicals. For example, U.S. Pat. No. 5,009,112 (the '112 patent) discloses a method and an apparatus for conducting field dissipation and leachate studies of test chemicals. Like Musgrave and his followers, the '112 patent requires intricate trenches and corresponding soil cores for collecting the leachate. Unlike Musgrave, the method in the '112 patent requires that the cores are left in place and a trench is dug next to the soil core to place the leachate collection means beneath the intact soil core. G. Richter and W. Jury have also documented work on chemical transport through soil in their paper entitled, "A Microlysimeter Field Study of Solute Transport through a Structure Sandy Loam." The Ricter and Jury method included obtaining a soil core, removing it, attaching a funnel to the end to collect the leachate and replacing the soil core. To obtain the leachate, the soil core was removed from the ground. Neither the '112 patent or Ricter and Jury collected the runoff.

With the evolving and ever increasing EPA requirements, a more dependable and complete analysis is required. On-site testing under the conditions which mimic the natural make-up of the soil, the soil and air temperature, the amount of precipitation as well as the actual dosage of the test chemical, is now necessary. The prior art methods discussed above simply do not address all these requirements. Furthermore, less expensive and time consuming procedures are desirable to reduce the cost of testing, even though more factors and parameters are being evaluated which would normally increase the testing expense. For example, the large trenches utilized in most of the prior art methods are expensive because the extensive excavation of soil requires disposal of large amounts of excavated soil. Then, at the end of the experiment, more expense is incurred to refill the trenches. The mere refilling is also undesirable due to potential impact on the surrounding environment due to settling soil and questionable soil stability. Less involved and drastic procedures, such as easily assembled, modular equipment, are also desirable to enable the test to be run in any type of terrain. It would be virtually impossible to use the prior art trench systems if the analysis were required on a mountain or hillside. Finally, due to the increasing use and advantage of radiolabeled test chemicals for experimental purposes to assess mobility and dissipation of chemicals, self-contained equipment is necessary to assure contamination of the surrounding soil and ground water does not occur.

Although each of the prior art methods and apparatus may have met the testing needs at the time, none of the prior art apparatus or test methods addresses each of these issues sufficiently for current day testing. Consequently, a need exists for a self-contained, modular unit and method for testing the mobility, dissipation, and degradation of chemicals and their degradates: in any type of terrain; in conjunction with radiolabeled test chemicals without contamination of the surrounding water and soil by the test chemical; with on-site testing under the conditions which simulate the natural conditions of the soil, the soil and air temperature, the amount of precipitation as well as the actual dosage of the test chemical; and finally, which affords a more dependable and complete analysis by assuring collection and the subsequent testing of the runoff, leachate and soil matrix.

SUMMARY OF THE INVENTION

The present invention comprises a self-contained, modular unit and method for evaluating the mobility, dissipation and degradation of chemicals and their degradates in a soil matrix. The modular styling of this invention assures that the unit can be used on-site in any type of terrain, thus simulating the natural conditions and make-up of the soil, the soil and air temperature, and precipitation, while using actual dosage proportions of the test chemical. The self-containment feature assists in assuring that contamination of surrounding soil and water by the radiolabeled test chemical normally used in conjunction with this invention does not occur. The self-contained, modular unit of this invention also affords the user of a more dependable and complete analysis by allowing collection of and the subsequent testing of the runoff, leachate and soil matrix.

The self-contained modular unit comprises at least a soil matrix vessel for surrounding the soil matrix and a leachate collection vessel communicating with the soil matrix vessel for collecting and storing the leachate from the soil matrix vessel. The leachate collection vessel is designed and connected to the soil matrix vessel in such a manner that the collected leachate is observable and removable from ground level, thus eliminating the necessity of digging a trench to view or retrieve the leachate as prior art units required. The preferred embodiment of the self-contained modular unit further comprises a runoff collection vessel which communicates with the soil matrix vessel for collection of the runoff from the soil matrix vessel. By collecting both the runoff and the leachate, the user has the opportunity to perform a more complete analysis of the degradation, horizontal runoff and vertical movement of the test chemicals and their degradates.

The method of evaluating the mobility, dissipation and degradation of chemicals and their degradates through a soil matrix involves the use of the self-contained modular unit of this invention, in conjunction with the following steps, including: obtaining a desired soil matrix in the soil matrix vessel; assembling the self-contained, soil matrix vessel; insuring the integrity of the soil matrix; assembling the self-contained modular unit; properly positioning the self-contained modular unit in the ground at the selected test site to simulate the natural make-up of the soil, soil and air temperature, and the natural precipitation; allowing the self-contained modular unit to acclimate to the test site; dosing the self-contained modular unit with the chemical to be tested; collecting the leachate and/or the runoff for the duration of the test; removing the self-contained, modular unit from the ground after the test is completed; and analyzing the leachate, runoff and the soil matrix.

DETAILED DESCRIPTION OF THE PREFERRED EMBODIMENT

A. The Self-Contained Modular Unit.

The present invention comprises a self-contained, modular unit and method for evaluating the mobility, dissipation and degradation of chemicals and their degradates through a soil matrix.

Figure 1:
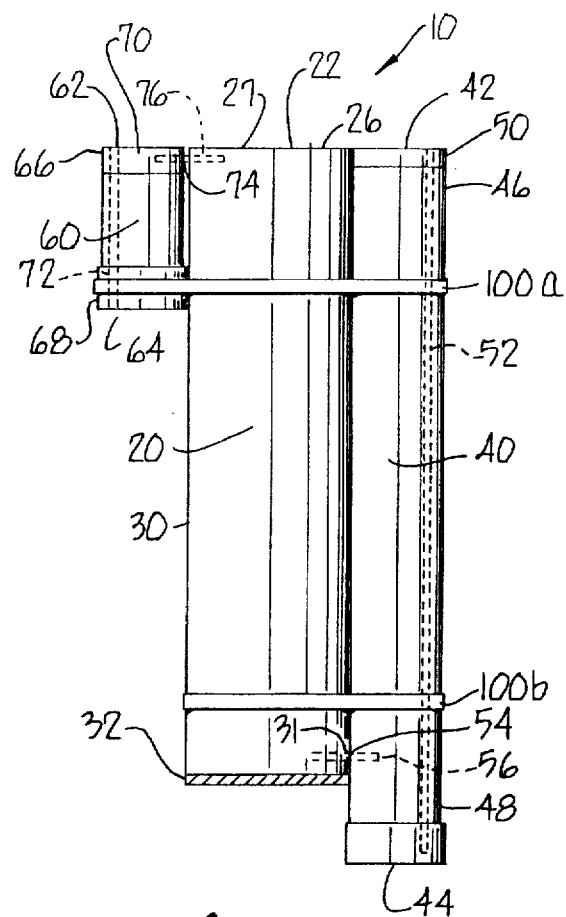
FIG. 1 is a perspective view of the self-contained, modular unit with both the runoff collection vessel and the leachate collection vessel attached to the soil matrix vessel.
Figure 5:
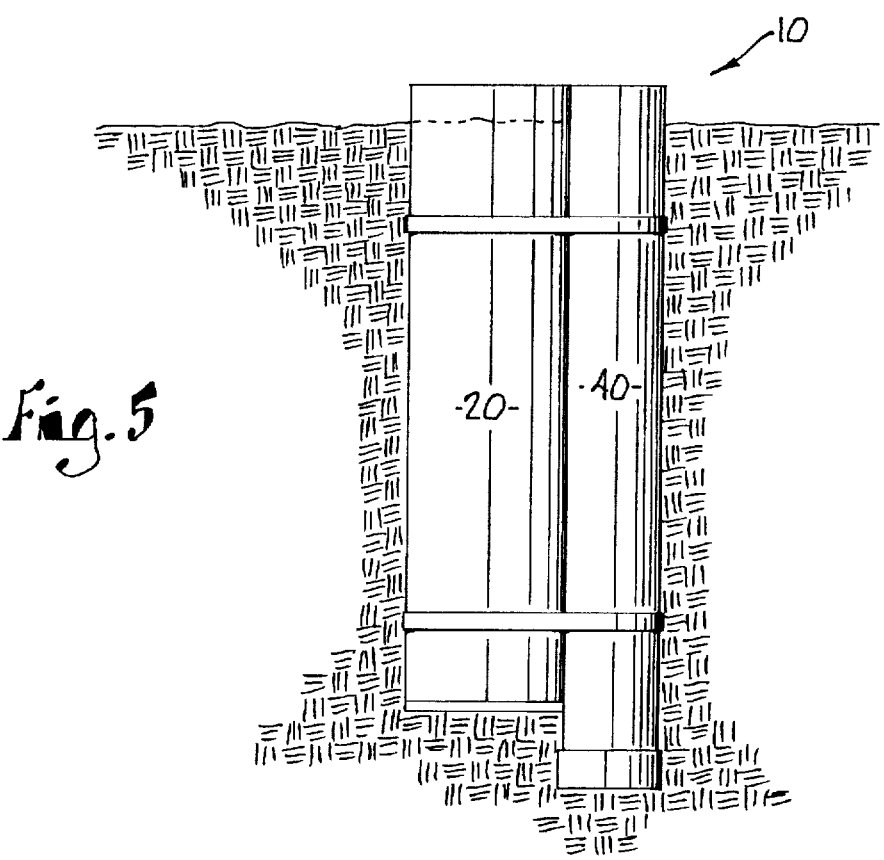
FIG. 5 is a perspective view of the alternative embodiment of this invention.

Referring to FIG. 1 in the preferred embodiment, self-contained, modular unit 10 is comprised of soil matrix vessel 20, leachate collection vessel 40, and runoff collection vessel 60. In an alternative embodiment of self-contained, modular unit 10, runoff collection vessel 60 is not utilized, although this is an undesirable embodiment when radiolabeled test chemicals are utilized. (See FIG. 5.)

1. Soil Matrix Vessel.

Figure 2:
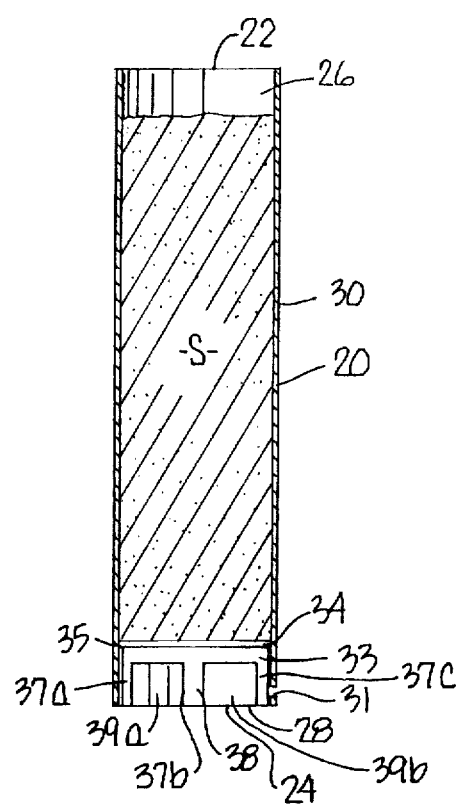
FIG. 2 is a cut-away view of the soil matrix vessel without the sealing cap.
Figure 3:
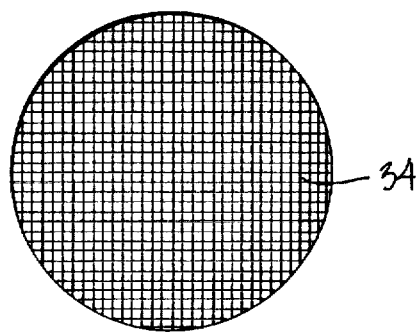
FIG. 3 is a top view of the sieve.

Referring to FIG. 2, before assembly, soil matrix vessel 20 is hollow and comprised of open top side 22, open bottom side 24, first end 26 adjacent open top side 22, second end 28 adjacent open bottom side 24 and mid section 30 located between first end 26 and second end 28. Sealing cap 32 (see FIG. 1) closes bottom side 24 of soil matrix vessel 20 after Soil Matrix S (see FIG. 2) is obtained. The manner in which sealing cap 32 is secured will be discussed more fully in the section below concerning assembling self-contained, modular unit 10.

Referring to FIG. 2, sieve 34 is placed below Soil Matrix S in soil matrix vessel 20. Sieve 34 is maintained in place by metal support plate 38 contacting sieve 34. Metal support plate 38 is hollow which allows Leachate L to pass through Soil Matrix S, sieve 34, and into second end 28 of soil matrix vessel 20. In FIG. 2, metal support plate 38 has support section 33, legs 37a–37c, and cutout sections 39a–b between legs 37. Alternative embodiments of metal support plate 38 could include any variation of a hollow pipe which would allow leachate to flow through Soil Matrix S and sieve 34 into second end 28 of soil matrix vessel 20. Metal support plate 38 as shown in FIG. 2 is preferred, because it does not require metal support plate 38 to include a leachate opening for Leachate L to flow from soil matrix vessel 20 into leachate collection vessel 40. Instead, cutout sections 39 are properly positioned to allow leachate to flow through leachate opening 31 in soil matrix vessel 20.

2. Leachate Collection Vessel.

Referring to FIG. 1, leachate collection vessel 40 is comprised of top side 42, sealed bottom side 44, first end 46 adjacent top side 42, and second end 48 adjacent sealed bottom side 44. Removable cap 50 seals top side 42 of leachate collection vessel 40 to assure contaminants, such as rain or runoff, do not enter leachate collection vessel 40. Hose 52 is used to remove Leachate L collected in leachate collection vessel 40. Leachate L is collected by removing removable cap 50 and drawing up by vacuum or other available means Leachate L through hose 52. Hose 52 is comprised of a material which reduces the possible contamination of or leaching of Leachate L by hose 52. These materials include high density polyethylene, high density polypropylene, Teflon or similar materials, with the preferred being Teflon.

Leachate L flows from soil matrix vessel 20 through leachate opening 31 and a leachate opening in sealing cap 32, if sealing cap 32 extends beyond leachate opening 31, through leachate flow member 56 into leachate opening 54 in leachate collection vessel 40. Leachate flow member 56, like hose 52, is comprised of a material for reducing possible contamination of or leaching of Leachate L by leachate flow member 56. These materials include high density polyethylene, high density polypropylene, Teflon or similar materials, with the preferred being Teflon.

In the preferred embodiment, at least a portion of the interior of second end 48 and sealed bottom side 44 of leachate collection vessel 40 is fitted with a material for reducing possible contamination of or leaching of Leachate L by leachate collection vessel 40. This material includes high density polyethylene or polypropylene, Teflon, silanized glass, or other similar materials with silanized glass being the preferred. For ease of assembly, instead of coating the interior of second end 48 and sealed bottom side 44 of leachate collection vessel 40, a silanized glass vessel 58 may be placed in leachate collection vessel 40 (see FIG. 4). If silanized glass vessel 58 is utilized, Leachate L can be retrieved from leachate collection vessel 40 by removing silanized glass vessel 58 from leachate collection vessel 40, collecting Leachate L, and replacing silanized glass vessel 58 in leachate collection vessel 40, or by vacuum via hose 52 as previously discussed in reference to FIG. 1.

Figure 4:
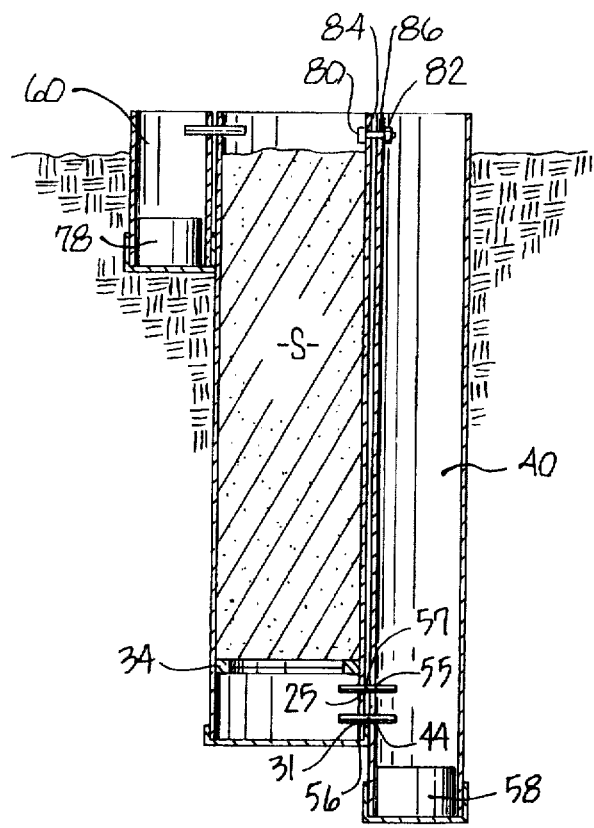
FIG. 4 is a perspective view of the self-contained, modular unit utilizing silanized glass vessels and two leachate openings.

Referring to FIG. 4, in an alternative embodiment, soil matrix vessel 20 includes second leachate opening 25. Leachate opening 31 is positioned in closer proximity to open bottom side 24 of soil matrix vessel 20. Leachate collection vessel 40 also includes second leachate opening 55 and second leachate flow member 57. Second leachate flow member 57 allows flow of Leachate L from soil matrix vessel 20 to leachate collection vessel 40, in the same manner described above in reference to leachate flow member 56. Second leachate flow member 57 is comprised of the same materials as leachate flow member 56.

The use of two leachate openings is desirable in some instances when a large amount of Leachate L is expected or when Soil Matrix S is very porous such that when it rains, or when water is applied to Soil Matrix S, the water, i.e. Leachate L moves through Soil Matrix S at such a high rate that only one leachate opening would be insufficient to assure immediate removal of Leachate L from soil matrix vessel 20. If backup of Leachate L were to occur in the soil matrix vessel 20, such that unremoved Leachate L contacted Soil Matrix S, saturation of Soil Matrix S would occur, thus defeating the integrity of the experiment. In this respect, second leachate opening 25 is positioned above leachate opening 31 to further assure undesirable saturation does not occur because removal of Leachate L is completed twice as fast through differently positioned leachate openings. The second leachate opening is also an assurance that Leachate L does not back up and thus saturate Soil Matrix S due to clogging of the lower leachate opening or flow member.

3. Runoff Collection Vessel.

Referring to FIG. 1, runoff collection vessel 60 is comprised of top side 62, sealed bottom side 64, first end 66 adjacent top side 62, and second end 68 adjacent sealed bottom side 64. Removable cap 70 seals top side 62 of runoff collection vessel 60 to assure contaminants, such as water and runoff from other sources than soil matrix vessel 20, do not enter runoff collection vessel 60. Hose 72 is used to remove Runoff R collected in runoff collection vessel 60. Runoff R is collected by removing removable cap 70 and drawing up Runoff R through hose 72 by vacuum or other means. Hose 72 is comprised of a material which reduces the possible contamination of or leaching of the leachate by hose 72. These materials include high density polyethylene, high density polypropylene, Teflon or similar materials, with the preferred being Teflon.

Runoff R flows from the surface of soil matrix vessel 20 through runoff flow member 76 and runoff opening 27 in soil matrix vessel 20, into runoff opening 74 (FIG. 1) in runoff collection vessel 60. Runoff flow member 76, like hose 72, is comprised of a material for reducing possible contamination of or leaching of Runoff R by runoff flow member 76. These materials include high density polyethylene, high density polypropylene, Teflon or similar materials, with the preferred being Teflon.

In the preferred embodiment, at least a portion of the interior of second end 68 and sealed bottom side 64 of runoff collection vessel 60 is fitted with a material for reducing possible contamination of or leaching of Runoff R by runoff collection vessel 60. These materials include high density polyethylene or polypropylene, Teflon, silanized glass, or other similar materials with silanized glass being the preferred. For ease of assembly, instead of coating the interior of second end 68 and sealed bottom side 64 of runoff collection vessel 60, a silanized glass vessel 78 may be placed in runoff collection vessel 60 (See FIG. 4). If silanized glass vessel 78 is utilized, runoff R can be retrieved from runoff collection vessel 60 by removing silanized glass vessel 78 from runoff collection vessel 60, collecting Runoff R, and replacing silanized glass vessel 78 in runoff collection vessel 60.

4. Material Make-up and Size.

Soil matrix vessel 20 is comprised of a material which is both sufficiently strong to withstand soil matrix vessel 20 being forced into the ground to obtain Soil Matrix S, and sufficiently impenetrable by water or other liquids to prohibit contaminants from entering soil matrix vessel 20 through sealing cap 32, first end 26, second end 28, or mid-section 30. These materials include steel, galvanized steel and pvc, with the preferred being steel.

Leachate collection vessel 40 and runoff collection vessel 60 are also comprised of a material which is sufficiently impenetrable by water or other liquids. These materials include PVC, high density polyethylene, acrylics and other plastics, with the preferred being PVC.

Soil matrix vessel 20 is normally circular in shape. The size of soil matrix vessel 20 is determined by the test site but is generally about 2 feet to about 5 feet long and about 6 inches to about 12 inches in diameter.

Leachate collection vessel 40 and runoff collection vessel 60 are normally circular. The size of both leachate collection vessel 40 and runoff collection vessel 60 are dictated by the test site, but generally runoff collection vessel 60 is shorter and leachate collection vessel 40 is longer due to the manner in which Runoff R and Leachate L are collected from soil matrix vessel 20. Standard sizes are about 4 inches to about 12 inches in diameter and about 2 feet to about 6 feet in length.

B. The Method of Using the Self-Contained Modular Unit.

The method of evaluating the mobility, dissipation and degradation of chemicals and their degradates through Soil Matrix S in conjunction with self-contained, modular unit 10 generally comprises the following steps: obtaining a desired Soil Matrix S in soil matrix vessel 20; assembling soil matrix vessel 20; insuring the integrity of Soil Matrix S; completing the assembly of and assuring the integrity of self-contained, modular unit 10; properly positioning self-contained, modular unit 10 in the ground at the test site to most accurately simulate natural conditions; allowing self-contained, modular unit 10 to acclimate to the test site; dosing self-contained, modular unit 10 with the chemical to be evaluated; collecting Leachate L and/or Runoff R for the duration of the test; removing self-contained, modular unit 10 from the ground after the test is completed; and analyzing Leachate L, Runoff R and Soil Matrix S to determine the mobility, dissipation and degradation of the test chemicals and their degradates.

1. Obtainin Soil Matrix S.

Obtaining the desired Soil Matrix S involves selecting a test site with similar soil and weather conditions, including temperature and rainfall, which the test chemical will be exposed to under normal conditions. The soil matrix is obtained by pressing soil matrix vessel 20 into the selected soil to obtain Soil Matrix S in soil matrix vessel 20. Although various techniques are available for pressing soil matrix vessel 20 into the ground, a backhoe is normally used.

2. Assembling Soil Matrix Vessel 20 and Checking Its Integrity.

To assemble soil matrix vessel 20, soil matrix vessel 20 is removed from the ground while Soil Matrix S is maintained inside soil matrix vessel 20. From open bottom side 24, approximately four to five inches of Soil Matrix S is removed. Sieve 34 is placed through open bottom side 24 of soil matrix vessel 20 in a position abutting Soil Matrix S. Metal support plate 38 is placed in soil matrix vessel 20 via open bottom side 24 in a position abutting sieve 34. Sieve 34 and metal support plate 38 are custom fit to soil matrix vessel 20 to assure Soil Matrix S is maintained in place and that Leachate L is forced through sieve 34 instead of seeping through an undesirable gap between the walls of soil matrix vessel 20 and sieve 34 or metal support plate 38. As discussed above, metal support plate 38 is positioned such that leachate opening 31 and second leachate opening 25 (if used) are not blocked.

Once metal support plate 38 is properly positioned, leachate flow member 56 and second leachate flow member 57 are fitted through and glued with silicone glue or other comparable materials respectively in leachate opening 31 and second leachate opening 25. (See FIG. 4.)

Sealing cap 32 is then placed over open bottom side 24 of soil matrix vessel. Sealing cap 32 is comprised of aluminum flashing, galvanized steel, steel sheet metal, or similar materials, with the preferred being aluminum flashing. Sealing cap 32 is sealed to soil matrix vessel 20 by first using silicone glue, then encircling soil matrix vessel 20 and sealing cap 32 with a hose clamp followed by duct tape (not shown). Those skilled in the art will recognize other sealing materials may also be used to effect a seal. If sealing cap 32 will cover leachate opening 31 and/or second leachate opening 25, a leachate opening (not shown) is drilled into sealing cap 32 before sealing cap 32 is attached to open bottom side 24.

The integrity of Soil Matrix S is tested by applying an excess amount of water to the surface of Soil Matrix S. The time in which it takes the water, i.e. Leachate L, to drain through Soil Matrix S is timed. If the flow through time is greater than a previously established test time, channeling is assumed, and soil matrix vessel 20 is disassembled and not used. The previously established test time is basically an average of all the test times. For example, for each test site, a plurality of self-contained, modular units 10 are utilized. The integrity of each Soil Matrix S is tested, and the test times are recorded. Each test time is then compared against the prior times, and if any test time is much faster than the previous test times, channeling is assumed, and the Soil Matrix S is not used.

3. Assembling Self-Contained Modular Unit 10 and Checking its Integrity.

After soil matrix vessel 20 is properly assembled and its integrity has been checked, leachate collection vessel 40 and, if used, runoff collection vessel 60 are physically attached to soil matrix vessel 20. Leachate flow member 56 and second leachate flow member 57 are fitted through and glued with silicone glue or other similar materials respectively to leachate opening 54 and second leachate opening 55 in leachate collection vessel 40. Galvanized bolt 80 (see FIG. 4) is then placed through opening 84 in first end 26 of soil matrix vessel 20 and opening 86 in first end 46 of leachate collection vessel 40 and maintained in place by nut 82 to more securely attach soil matrix vessel 20 to leachate collection vessel 40. Runoff flow member 76 is also fitted and glued with silicone glue or other similar materials to runoff opening 27 in soil matrix vessel 20 and runoff opening 74 in runoff collection vessel 60. Duct tape 100a, 100b (see FIG. 1) or other similar adhesive materials encircle self-contained, modular unit 10 and securely fastens runoff collection vessel 60 and leachate collection vessel 40 to soil matrix vessel 20.

Before assembling self-contained, modular unit 10, if silanized vessels 58 and 78 are utilized, they are placed in leachate collection vessel 40 and runoff collection vessel 60 respectively. If used, hoses 52 and 72 are placed in leachate collection vessel 40 and runoff collection vessel 60, respectively, upon assembly.

After self-contained, modular unit 10 is properly assembled, the integrity of self-contained, modular unit 10 is tested. Leachate flow member 56 and runoff flow member 76 are checked for blockage by adding water to Soil Matrix vessel 20 and collecting the Runoff R and Leachate L. Once confirming runoff flow member 76 is in proper working order, and Soil Matrix S is not channeled, then self-contained, modular unit 10 is ready to be placed at the test site.

4. Positioning Self-Contained, Modular Unit 10.

Dependent on the experimental parameters, the test site is normally the same site at which the soil matrix was obtained. In fact, self-contained, modular unit 10 will normally be placed back into the same hole or area from which Soil Matrix S was obtained. To accommodate the larger self-contained, modular unit 10, the area from which the Soil Matrix S was obtained is dug out. Self-contained, modular unit 10 is positioned such that the surface of Soil Matrix S is approximately even with the soil line. (See FIG. 4.) In this manner, the actual temperature of the soil is most adequately simulated. Otherwise, if the surface of Soil Matrix S was above the soil line, the amount of water that either runs off or is absorbed into Soil Matrix S could be adversely affected because the natural conditions were not accurately simulated. Once the entire self-contained, modular unit 10 is in the ground at the proper level, dirt is backfilled and the top soil is replaced around the area which was previously disturbed. The replacement of the top soil also assures the natural conditions are simulated. Each self-contained, modular unit 10 utilized is positioned in this manner.

Due to the use of radiolabeled chemicals and to further assure that the radiolabeled chemicals do not contaminate soil and water beyond the test site, a metal barrier is constructed around the test site. Metal flashing, approximately one and one-half feet wide, is placed approximately eight to twelve inches into the ground around the test site. This not only avoids contamination of the soil outside of the test site, but also assures that extra water does not come into the test site.

5. Acclimation of Self-Contained, Modular Unit 10.

After assembly and positioning, self-contained, modular unit 10 is allowed to acclimate to its surroundings by being exposed to natural conditions for approximately 30 days or less, dependent on the soil. The acclimation period assures that self-contained, modular unit 10 has properly acclimated to its surroundings. For example, as stated above, Soil Matrix S must be allowed to reach the same temperature under the same climatic conditions as the surrounding soil to assure test integrity.

6. Dosing of Self-Contained, Modular Unit 10.

Once the acclimation period is complete, self-contained, modular unit 10 is dosed with a radiolabeled test chemical. The most common manner in which to label the chemical is to use the carbon $^{14}$C. isotope. The use of $^{14}$C. isotope enables the user to trace not only the test chemical but also its degradates effectively. The size of the dosage is normally dependent on the quantity of the agrochemical which will be used under normal conditions. Although in some test situations, an exaggerated rate of test chemical may be used to test the effects of metabolites whose concentration may be multiplied due to a condensed end product. For example, approximately 100 bushels of peanuts are required to make one ounce of peanut oil. Although a pesticide or agrochemical may not have adverse affects at the 100 bushel rate, it may very well have adverse affects at the one ounce peanut oil rate. Multiple applications may also be utilized throughout the experiment dependent on the design of the experiment.

Before self-contained, modular unit 10 is dosed with the radiolabeled test chemical, all Leachate L from leachate collection vessel 40 and Runoff R from runoff collection vessel 60 is removed to avoid contamination of the test chemical mediated leachate production. After being dosed, all Runoff R and Leachate L from self-contained, modular unit 10, is collected and tested. Leachate L and Runoff R are normally collected on a weekly basis. If a heavy rain occurs, then Leachate L and Runoff R may be collected on a more periodic basis to assure Leachate L or Runoff R does not overflow and thus saturate Soil Matrix M. Leachate L and Runoff R are collected in dark bottles, maintained on dry ice and immediately sent to the lab for testing. This assures further breakdown of the test chemical or its degradates which are in Leachate L or Runoff R does not occur.

7. Removal & Analysis.

Leachate L and Runoff R are initially tested using a scintillation counter to determine if any radiolabeled material is in Runoff R or Leachate L. If the scintillation counter detects radiolabeled material, further techniques such as HPLC, TLC, GPC, GC and other methods are used to analyze Leachate L and Runoff R.

After the test has been completed, remaining Runoff R and Leachate L is removed from self-contained, modular unit 10 and forwarded to the laboratory for analysis. Self-contained, modular unit 10 is then removed from the ground and partially disassembled on site. The on-site disassembly includes removing leachate flow member 56 and caulking leachate opening 54 in leachate collection vessel 40 and runoff opening 74 in runoff collection vessel 60. Soil matrix vessel 20 is then wrapped with double plastic wrap and placed in an ice chest under dry ice. This assures almost an instantaneous freeze of Soil Matrix S which assures no further instantaneous freeze of Soil Matrix S which assures no further breakdown of the chemicals in Soil Matrix S.

Soil matrix vessel 20 with frozen Soil Matrix S is then shipped to the laboratory for analysis. Soil matrix vessel 20 is cut in pre-selected sizes while Soil Matrix S is still frozen. Each individually cut section is then tested. The following testing procedure is completed on each individual section of Soil Matrix S. Soil matrix vessel 20 is removed from around Soil Matrix S and/or Soil Matrix S remaining in the cut section of soil matrix vessel 20 in the segment is scooped out. Soil Matrix S is placed into a mill with dry ice and ground to a fine powder approximately <2mm.

This procedure is completed under dry ice to assure the integrity of the samples and assure no further breakdown of the chemical and/or degradates occurs. The ground materials are then extracted, with the extract materials tested via the previous mentioned techniques used in conjunction with the Leachate L and Runoff R.

After all testing procedures are completed, a radioactive mass accountability is run to assure all radiolabeled materials have been retrieved.

EXAMPLE 1

Upon arrival at the laboratory, the leachate samples are filtered and then analyzed for the compound of interest by a specific analytical method of an analysis. Samples containing radioactivity are analyzed with a liquid scintillation counter. An aliquot of the sample is placed into a scintillation vial. An appropriate amount of liquid scintillation cocktail is added. The vial is capped, shaken and counted from 2–5 minutes and total radiocarbon determined. If warranted, the leachate samples may be analyzed by high performance liquid chromatography (HPLC) or thin layer chromatography (TLC) to characterize and quantirate the radioactivity of the compound in the sample.

EXAMPLE 2

Upon arrival at the laboratory, the runoff samples are filtered and then analyzed for the compound of interest by a specific analytical method of an analysis. Samples containing radioactivity are analyzed with a liquid scintillation counter. An aliquot of the sample is placed into a scintillation vial. An appropriate amount of liquid scintillation cocktail is added. The vial is capped, shaken and counted from 2–5 minutes and total radiocarbon determined. If warranted, the runoff samples may be analyzed by high performance liquid chromatography (HP LC) or thin layer chromatography (TLC) to characterize and quantirate the radioactivity of the compound in the sample.

EXAMPLE 3

Upon arrival at the laboratory, the frozen soil cores will be sectioned into increments (i.e., 0–6", 6–12", etc.) with a hand saw or equivalent methodology. The increments will be stored frozen if not immediately needed for analysis. The soil from each segment will be further processed by homogenizing with dry ice in mill or other appropriate device. The homogenization will continue until the soil is ground to a fine texture and then placed in bottles until analyzed.

The total radioactivity of the soil will be determined by combustion analysis. Triplicate aliquots of soil will be combusted using an automatic sample analyzer. The radioactive $CO_2$ will be trapped in scintillation cocktail and quantitated by liquid scintillation counting. If warranted, the soil samples may be extracted and analyzed by high performance liquid chromatography (HPLC) or thin layer chromatography (TLC) to characterize and quantitate the radioactivity of the compound in the sample.

If the radioactivity quantitated in the leachate, runoff or soil samples is such that structural confirmation of degradates is necessary, then those samples will be analyzed by mass spectroscopy.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

What is claimed and desired to be secured by Letters Patent is as follows:

1. A self-contained, three modular unit for evaluating the mobility, dissipation and degradation of chemicals and their degradates through a soil matrix, comprising:
   a. a soil matrix vessel for surrounding said soil matrix;
   b. a runoff collection vessel communicating with said soil matrix vessel for collecting and storing the runoff from said soil matrix vessel;
   c. a leachate collection vessel communicating with said soil matrix vessel for collecting and storing the leachate from said soil matrix vessel; and wherein
   d. said soil matrix vessel is hollow and comprised of,
      i. an open top side,
      ii. an open bottom side which is sealed by a sealing cap after said soil matrix is obtained,
      iii. a first end adjacent said top side,
      iv. a second end adjacent said bottom side, and
      v. a midsection between said first end and said second end wherein said soil matrix is located;
   e. said runoff collection vessel is hollow and comprised of,
      i. a top side sealable with a removable cap,
      ii. a sealed bottom side,
      iii. a first end adjacent said top side, and
      iv. a second end adjacent said bottom side;
   f. said leachate collection vessel is hollow and comprised of,
      i. a top side sealable with a removable cap,
      ii. a sealed bottom side,
      iii. a first end adjacent said top side, and
      iv. a second end adjacent said bottom side;
   g. said first end of said soil matrix vessel having at least one runoff opening for said runoff to exit said soil matrix vessel;

h. said runoff collection vessel having at least one runoff opening for receiving said runoff exiting from said soil matrix vessel; and i. a runoff flow member connecting said runoff opening in said first end of said soil matrix vessel to said runoff opening in said runoff collection vessel such that said runoff flows from said soil matrix vessel to said runoff collection vessel.

2. The self-contained, three modular unit of claim 1, further comprising a sieve, fixedly secured in said soil matrix vessel beneath said soil matrix and above said leachate opening in said second end of said soil matrix vessel for assuring portions of said soil matrix do not block said leachate opening in said soil matrix vessel.

3. The self-contained, three modular unit of claim 2, wherein said top side of said soil matrix vessel and said runoff opening in said first end of said soil matrix vessel are selectively positioned above ground level to imitate natural runoff conditions and avoid unnatural pooling of runoff on the surface of said soil matrix.

4. The self-contained, three modular unit of claim 3, wherein said soil matrix vessel is comprised of a material which is
   a. sufficiently strong to withstand said soil matrix vessel being forced into the ground to obtain said soil matrix; and
   b. sufficiently impenetrable by water or other liquids to prohibit contaminants from entering said soil matrix vessel through said sealing cap, said first end, said second end or said midsection.

5. The self-contained, three modular unit of claim 4, wherein said runoff collection vessel and said leachate collection vessel are comprised of a material which is sufficiently impenetrable by water or other liquids.

6. A self-contained, three modular unit for evaluating the mobility, dissipation and degradation of chemicals and their degradates through a soil matrix, comprising:
   a. a soil matrix vessel for surrounding said soil matrix;
   b. a runoff collection vessel communicating with said soil matrix vessel for collecting and storing the runoff from said soil matrix vessel;
   c. a leachate collection vessel communicating with said soil matrix vessel for collecting and storing the leachate;
   d. said soil matrix vessel is hollow and comprised of,
      i. an open top side,
      ii. an open bottom side which is sealed by a sealing cap after said soil matrix is obtained,
      iii. a first end adjacent said top side,
      iv. a second end adjacent said bottom side, and
      v. a midsection between said first end and said second end wherein said soil matrix is located;
   e. said runoff collection vessel is hollow and comprised of,
      i. a top side sealable with a removable cap,
      ii. a sealed bottom side,
      iii. a first end adjacent said top side, and
      iv. a second end adjacent said bottom side;
   f. said leachate collection vessel is hollow and comprised of,
      i. a top side sealable with a removable cap,
      ii. a sealed bottom side,
      iii. a first end adjacent said top side, and
      iv. a second end adjacent said bottom side;
   g. said first end of said soil matrix vessel having at least one runoff opening for said runoff to exit said soil matrix vessel;
   h. said runoff collection vessel having at least one runoff opening for receiving said runoff exiting from said soil matrix vessel;
   i. a runoff flow member connecting said runoff opening in said first end of said soil matrix vessel to said runoff opening in said runoff collection vessel such that said runoff flows from said soil matrix vessel to said runoff collection vessel;
   j. said second end of said soil matrix vessel having at least one leachate opening positioned for said leachate to exit said soil matrix vessel;
   k. said leachate collection vessel having at least one leachate opening for receiving said leachate exiting from said soil matrix vessel; and
   l. a leachate flow member connecting said leachate opening in said second end of said soil matrix vessel and said leachate opening in said leachate collection vessel for allowing said leachate to flow from said soil matrix vessel to said leachate collection vessel.

7. The self-contained, three modular unit of claim 6, further comprising
   a. a sieve, fixedly secured in said soil matrix vessel beneath said soil matrix and above said leachate opening in said second end of said soil matrix vessel for assuring portions of said soil matrix do not block said leachate opening in said soil matrix vessel; and
   b. when in use, said top side of said soil matrix vessel and said runoff opening in said first end of said soil matrix vessel are selectively positioned above ground level to imitate natural runoff conditions and avoid unnatural pooling of runoff on the surface of said soil matrix.

8. The self-contained, three modular unit of claim 7, wherein
   a. said soil matrix vessel is comprised of a material which is
      i. sufficiently strong to withstand said soil matrix vessel being forced into the ground to obtain said soil matrix; and
      ii. sufficiently impenetrable by water or other liquids to prohibit contaminants from entering said soil matrix vessel through said sealing cap, said first end, said second end or said midsection; and
   b. said runoff collection vessel and said leachate collection vessel are comprised of a material which is sufficiently impenetrable by water or other liquids.

9. The self-contained, three modular unit of claim 8, wherein at least a portion of said second end and said bottom side of said runoff collection vessel and at least a portion of said second end and said bottom side of said leachate collection vessel are fitted with a material for reducing possible contamination of or leaching of said runoff by said runoff collection vessel and said leachate collection vessel.

10. A method of evaluating the mobility, dissipation and degradation of chemicals and their degradates through a soil matrix, comprising the steps of:
   a. obtaining a desired soil matrix in a soil matrix vessel;
   b. insuring the integrity of said soil matrix;
   c. assembling a self-contained, modular unit for evaluating said soil matrix, said self-contained, modular unit comprised of,
      i. said soil matrix vessel;
      ii. a leachate collection vessel communicating with said soil matrix vessel for collecting and storing the leachate from said soil matrix vessel;
      iii. a runoff collection vessel communicating with said soil matrix vessel for collecting and storing the runoff from said soil matrix vessel;

iv. said soil matrix vessel is hollow and comprises,
  aa. an open top side,
  bb. an open bottom side which is sealed by a sealing cap during assembly of said self-contained modular unit,
  cc. a first end adjacent said top side,
  dd. a second end adjacent said bottom side, and
  ee. a midsection between said first end and said second end wherein said soil matrix is located;
v. said leachate collection vessel is hollow and comprises,
  aa. a top side sealable with a removable cap,
  bb. a sealed bottom side,
  cc. a first end adjacent said top side, and
  dd. a second end adjacent said bottom side;
vi. said soil matrix vessel having at least one leachate opening positioned beneath said soil matrix for said leachate to exit said soil matrix vessel;
vii. said leachate collection vessel having at least one leachate opening for receiving said leachate exiting from said soil matrix vessel;
viii. a leachate flow member connecting said leachate opening in said second end of said soil matrix vessel and said leachate opening in said leachate collection vessel for allowing said leachate to flow from said soil matrix vessel to said leachate collection vessel;
ix. said runoff collection vessel is hollow and comprised of,
  aa. a top side sealable with a removable cap,
  bb. a sealed bottom side,
  cc. a first end adjacent said top side, and
  dd. a second end adjacent said bottom side;
x. said first end of said soil matrix vessel having at least one runoff opening above said soil matrix for said runoff to exit said soil matrix vessel;
xi. said runoff collection vessel having at least one runoff opening for receiving said runoff exiting from said soil matrix vessel;
xii. a runoff flow member connecting said runoff opening in said first end of said soil matrix vessel and said runoff opening in said runoff collection vessel for allowing said runoff to flow from said soil matrix vessel to said runoff collection vessel; and
xii. a sieve fixedly secured beneath said soil matrix and above said leachate opening in said soil matrix vessel for assuring portions of said soil matrix do not block said leachate opening in said soil matrix vessel;
d. positioning said self-contained modular unit into the ground at the test site such that said top side of said soil matrix vessel and said runoff opening in said first end of said soil matrix vessel are selectively positioned above ground level to imitate natural runoff conditions and avoid unnatural pooling of runoff on the surface of said soil matrix;
e. allowing said self-contained modular unit to acclimate to said test site;
f. dosing said self-contained modular unit with the chemical to be tested;
g. collecting said leachate for the duration of said test;
h. removing said self-contained modular unit from said ground after said test is completed; and
i. analyzing said leachate, said runoff and said soil matrix.

11. A self-contained, modular unit for evaluating the mobility, dissipation and degradation of chemicals and their degradates through a soil matrix, comprising:
a. a soil matrix vessel for surrounding said soil matrix;
b. a leachate collection vessel communicating with said soil matrix vessel for collecting and storing the leachate from said soil matrix vessel such that said leachate is observable and removable from ground level;
c. said soil matrix vessel is hollow and comprises,
  i. and open top side,
  ii. an open bottom side which is sealed by a sealing cap after said soil matrix is obtained,
  iii. a first end adjacent said top side,
  iv. a second end adjacent said bottom side, and
  v. a midsection between said first end and said second end wherein said soil matrix is located;
d. said leachate collection vessel is hollow and comprises,
  i. a top side sealable with a removable cap,
  ii. a sealed bottom side,
  iii. a first end adjacent said top side, and
  iv. a second end adjacent said sealed bottom side;
e. said soil matrix vessel having at least one leachate opening positioned beneath said soil matrix for said leachate to exit said soil matrix vessel;
f. said leachate collection vessel having at least one leachate opening for receiving said leachate exiting from said soil matrix vessel;
g. a leachate flow member connected between said leachate opening in said second end of said soil matrix vessel and said leachate opening in said leachate collection vessel for allowing said leachate to flow from said soil matrix vessel to said leachate collection vessel, and further comprising a runoff collection vessel communicating with said soil matrix vessel for collecting and storing the runoff from said soil matrix vessel, wherein
h. said runoff collection vessel is hollow and comprised of,
  i. a top side sealable with a removable cap,
  ii. a sealed bottom side,
  iii. a first end adjacent said top side, and
  iv. a second end adjacent said bottom side;
i. said first end of said soil matrix vessel having at least one runoff opening above said soil matrix for said runoff to exit said soil matrix vessel;
j. said runoff collection vessel having at least one runoff opening for receiving said runoff exiting from said soil matrix vessel; and
k. a runoff flow member connecting said runoff opening in said first end of said soil matrix vessel and said runoff opening in said runoff collection vessel for allowing said runoff to flow from said soil matrix vessel to said runoff collection vessel.

12. A method of evaluating the mobility, dissipation and degradation of chemicals and their degradates through a soil matrix, comprising the steps of:
a. obtaining a desired soil matrix in a soil matrix vessel;
b. assembling a self-contained, modular unit for evaluating said soil matrix, said self-contained, modular unit comprised of,
  i. said soil matrix vessel, and
  ii. a leachate collection vessel con ununicating with said soil matrix vessel fro collecting and storing the leachate from said soil matrix vessel such that said leachate is observable and removable from ground level when said self-contained, modular unit is positioned in the ground during the testing procedure;
c. insuring the integrity of said soil matrix in said self-contained modular unit;

d. placing said self-contained modular unit into the ground at the test site;

e. allowing said self-contained modular unit to acclimate to said test site;

f. dosing said self-contained modular unit with the chemical to be tested;

g. collecting said leachate for the duration of said test;

h. removing said self-contained, modular unit from said ground after said test is completed;

i. analyzing said leachate and said soil matrix; and wherein j. said soil matrix vessel is hollow and comprises,
 i. an open top side,
 ii. an open bottom side which is sealed by a sealing cap during assembly of said self-contained, modular unit,
 iii. a first end adjacent said top side,
 iv. a second end adjacent said bottom side, and
 v. a midsection between said first end and said second end wherein said soil matrix is located;

k. said leachate collection vessel is hollow and comprises,
 i. a top side sealable with a removable cap,
 ii. a sealed bottom side,
 iii. a first end adjacent said top side, and
 iv. a second end adjacent said bottom side;

l. said soil matrix vessel having at least one leachate opening positioned beneath said soil matrix for said leachate to exit said soil matrix vessel;

m. said leachate collection vessel having at least one leachate opening for receiving said leachate exiting from said soil matrix vessel;

n. a leachate flow member connecting said leachate opening in said second end of said soil matrix vessel and said leachate opening in said leachate collection vessel for allowing said leachate to flow from said soil matrix vessel to said leachate collection vessel;

o. a sieve fixedly secured beneath said soil matrix and above said leachate opening in said soil matrix vessel for assuring portions of said soil matrix do not block said leachate opening in said soil matrix vessel; and wherein said self-contained, modular unit further comprises a runoff collection vessel, p. said runoff collection vessel is hollow and comprised of,
 i. a top side sealable with a removable cap,
 ii. a sealed bottom side,
 iii. a first end adjacent said top side, and
 iv. a second end adjacent said bottom side;

q. said first end of said soil matrix vessel having at least one runoff opening above said soil matrix for said runoff to exit said soil matrix vessel;

r. said runoff collection vessel having at least one runoff opening for receiving said runoff exiting from said soil matrix vessel;

s. a runoff flow member connecting said runoff opening in said first end of said soil matrix vessel and said runoff opening in said runoff collection vessel for allowing said runoff to flow from said soil matrix vessel to said runoff collection vessel; and t. said self-contained, modular unit is selectively positioned in said ground such that said top side of said soil matrix vessel and said runoff opening in said first end of said soil matrix vessel are selectively positioned about ground level to imitate natural runoff conditions and avoid unnatural pooling of runoff on the surface of said soil matrix.

13. A self-contained, modular lysimeter for evaluating the mobility, dissipation and degradation of chemicals and their degradates through a soil matrix, comprising:

a. a first vessel having a hollow construction and having a capped bottom end, said first vessel for receiving a soil matrix;

b. said first vessel bottom end having a screen mounted upwardly thereof and means forming a chamber in said bottom and for receiving leachate dissipated through said soil matrix;

c. a second vessel of hollow construction and having capped top and bottom ends, said second vessel for receiving and collecting leachate from said first vessel;

d. means joining said first and second vessels together in contacting side-by-side relationships to comprise a modular structure, said means being connectible and disconnectible to join and separate said first and second vessels from one another; and e. a flow conduit extending from said first vessel from said chamber in the bottom thereof to said second vessel above its bottom end to form a reservoir, whereby said leachate flows from said first vessel and collects in said reservoir in said second vessel.

14. A self-contained, modular lysimeter for evaluating the mobility, dissipation and degradation of chemicals and their degradates through a soil matrix, comprising:

a. a first vessel of hollow construction and having a capped bottom end, said first vessel for receiving a soil matrix;

b. a second vessel of hollow construction and having capped top and bottom ends, said second vessel for collecting and storing leachate;

c. means joining said first and second vessels together in contacting side-by-side relationship to comprise a modular structure, said means being connectible and disconnectible to join and separate said first and second vessels one from the other; and d. a flow conduit extending from said first vessel adjacent its said bottom end to said second vessel above its said bottom end, whereby said leachate flows from said first vessel and collects in a reservoir at said bottom end of said second vessel.

15. A self-contained, modular lysimeter for placing upright in the soil and for evaluating the mobility, dissipation and degradation of chemicals and their degradates through a soil matrix, comprising:

a. a first vessel having a hollow construction and having a top end and a capped bottom end, said first vessel for receiving a soil matrix;

b. a second vessel of hollow construction and having capped top and bottom ends, said second vessel for collecting and storing leachate;

c. a third vessel of hollow construction and having capped top and bottom ends, said third vessel for collecting and storing runoff water from said first vessel;

d. means joining said first, second and third vessels together in contacting, side-by-side relationship to form a modular structure, said means being connectible and disconnectible to separate said vessels each from the other;

e. a first flow conduit extending from said first vessel adjacent its bottom end to said second vessel above its bottom end, whereby said leachate flows from said first vessel and collects in a reservoir at said bottom end of said second vessel; and f. a second flow conduit extending from said first vessel adjacent its top end to said third vessel adjacent its top end, whereby runoff water flows from said first vessel and collects in said third vessel.

* * * * *